United States Patent
Lee et al.

(10) Patent No.: US 8,500,730 B2
(45) Date of Patent: Aug. 6, 2013

(54) CATHETER WITH OMNI-DIRECTIONAL OPTICAL TIP HAVING ISOLATED OPTICAL PATHS

(75) Inventors: James K. Lee, San Mateo, CA (US); Chad Allen Lieber, Chino Hills, CA (US); Michael Olen Zirkle, Fullerton, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 1111 days.

(21) Appl. No.: 11/941,884

(22) Filed: Nov. 16, 2007
(Under 37 CFR 1.47)

(65) Prior Publication Data

US 2009/0131931 A1 May 21, 2009

(51) Int. Cl.
*A61B 18/14* (2006.01)

(52) U.S. Cl.
USPC .................................................. 606/41

(58) Field of Classification Search
USPC .............. 606/2–16, 41, 45–50; 607/101–105
See application file for complete search history.

(56) References Cited

U.S. PATENT DOCUMENTS

| | | |
|---|---|---|
| 1,791,794 A | 2/1931 | Chesney |
| 4,469,098 A | 9/1984 | Davi |
| 4,587,972 A | 5/1986 | Morantte, Jr. |
| 4,669,098 A | 5/1987 | Boatwright |
| 4,669,467 A * | 6/1987 | Willett et al. ............ 606/7 |
| 4,672,961 A | 6/1987 | Davies |
| 4,736,743 A | 4/1988 | Daikuzono |
| 4,819,632 A | 4/1989 | Davies |
| 4,860,743 A | 8/1989 | Abela |
| 5,041,109 A | 8/1991 | Abela |
| 5,061,265 A | 10/1991 | Abela et al. |
| 5,147,348 A | 9/1992 | Leckrone et al. |

(Continued)

FOREIGN PATENT DOCUMENTS

| | | |
|---|---|---|
| EP | 0 441 040 A2 | 8/1991 |
| EP | 0 195 375 A | 9/1999 |

(Continued)

OTHER PUBLICATIONS

European Patent Search Report of European Patent Application EP 08 25 3725 dated Apr. 22, 2009.

(Continued)

*Primary Examiner* — Michael Peffley
*Assistant Examiner* — Khadijeh Vahdat
(74) *Attorney, Agent, or Firm* — Christie, Parker & Hale, LLP

(57) ABSTRACT

A catheter enables real-time light measurements from tissue while performing RF ablation. The tip design isolates illumination and collection paths such that light exits the tip and travels through the tissue before returning to the tip. The catheter has a tip electrode having an exterior shell, an inner layer and a hollow cavity. The inner layer is configured to transmit light outside the tip electrode, and the hollow cavity is configured to receive light. An inner surface of the inner layer has an opaque coating to isolate light injected into the inner layer from light collected in the hollow cavity. A first optical waveguide extends between the catheter body and tip electrode to inject light into the inner layer and illuminate the tissue, and a second optical waveguide extends between the catheter body and tip electrode to collect the recaptured light in the hollow cavity.

29 Claims, 13 Drawing Sheets

U.S. PATENT DOCUMENTS

| | | | |
|---|---|---|---|
| 5,151,096 A * | 9/1992 | Khoury | 606/15 |
| 5,248,311 A | 9/1993 | Black et al. | |
| 5,267,996 A | 12/1993 | Fletcher | |
| 5,370,608 A | 12/1994 | Sahota et al. | |
| 5,370,640 A | 12/1994 | Kolff | |
| 5,391,199 A | 2/1995 | Ben-Haim | |
| 5,443,489 A | 8/1995 | Ben-Haim | |
| 5,480,422 A | 1/1996 | Ben-Haim | |
| 5,546,951 A | 8/1996 | Ben-Haim | |
| 5,558,091 A | 9/1996 | Acker et al. | |
| 5,568,809 A | 10/1996 | Ben-haim | |
| 5,630,809 A | 5/1997 | Connor | |
| 5,643,253 A | 7/1997 | Baxter et al. | |
| 5,688,264 A | 11/1997 | Ren et al. | |
| 5,693,043 A | 12/1997 | Kittrell et al. | |
| 5,807,248 A | 9/1998 | Mills | |
| 5,807,389 A | 9/1998 | Gardetto et al. | |
| 5,830,209 A | 11/1998 | Savage et al. | |
| 5,861,020 A | 1/1999 | Schwarzmaier | |
| 5,964,757 A | 10/1999 | Ponzi | |
| 5,997,571 A | 12/1999 | Farr et al. | |
| 6,016,452 A | 1/2000 | Kasevich | |
| 6,053,912 A * | 4/2000 | Panescu et al. | 606/40 |
| 6,071,302 A | 6/2000 | Sinofsky et al. | |
| 6,106,516 A | 8/2000 | Massengill | |
| 6,120,476 A * | 9/2000 | Fung et al. | 604/95.04 |
| 6,143,018 A | 11/2000 | Beuthan et al. | |
| 6,168,594 B1 | 1/2001 | LaFontaine et al. | |
| 6,171,275 B1 | 1/2001 | Webster, Jr. | |
| 6,171,303 B1 | 1/2001 | Ben-Haim et al. | |
| 6,241,666 B1 | 6/2001 | Pomeranz et al. | |
| 6,423,055 B1 | 7/2002 | Farr et al. | |
| 6,464,694 B1 | 10/2002 | Massengill | |
| 6,468,260 B1 | 10/2002 | Bumbalough et al. | |
| 6,579,285 B2 | 6/2003 | Sinofsky | |
| 6,602,242 B1 * | 8/2003 | Fung et al. | 604/528 |
| 6,692,486 B2 | 2/2004 | Jaafar et al. | |
| 6,736,808 B1 | 5/2004 | Motamedi et al. | |
| 6,923,805 B1 | 8/2005 | LaFontaine et al. | |
| 6,953,457 B2 | 10/2005 | Farr et al. | |
| 2001/0012429 A1 | 8/2001 | Wach et al. | |
| 2002/0022834 A1 * | 2/2002 | Simpson et al. | 606/32 |
| 2002/0026188 A1 * | 2/2002 | Balbierz et al. | 606/41 |
| 2002/0045848 A1 | 4/2002 | Jaafar et al. | |
| 2002/0183729 A1 | 12/2002 | Farr et al. | |
| 2003/0004506 A1 | 1/2003 | Messing | |
| 2003/0040657 A1 | 2/2003 | Yamaya | |
| 2003/0125730 A1 | 7/2003 | Berube et al. | |
| 2004/0015061 A1 | 1/2004 | Currier et al. | |
| 2004/0015138 A1 | 1/2004 | Currier et al. | |
| 2004/0158302 A1 | 8/2004 | Chornenky et al. | |
| 2005/0059962 A1 | 3/2005 | Phan et al. | |
| 2005/0065504 A1 * | 3/2005 | Melsky et al. | 606/16 |
| 2005/0070894 A1 | 3/2005 | McClurken | |
| 2005/0096643 A1 | 5/2005 | Brucker et al. | |
| 2005/0143721 A1 | 6/2005 | Brucker et al. | |
| 2005/0143722 A1 | 6/2005 | Brucker et al. | |
| 2005/0159734 A1 | 7/2005 | Brucker et al. | |
| 2005/0165462 A1 * | 7/2005 | Bays et al. | 607/88 |
| 2005/0171520 A1 | 8/2005 | Farr et al. | |
| 2005/0222557 A1 * | 10/2005 | Baxter et al. | 606/16 |
| 2005/0267452 A1 | 12/2005 | Farr et al. | |
| 2006/0122587 A1 | 6/2006 | Sharareh | |
| 2006/0184165 A1 | 8/2006 | Webster, Jr. et al. | |
| 2007/0287998 A1 * | 12/2007 | Sharareh et al. | 606/41 |
| 2008/0097220 A1 * | 4/2008 | Lieber et al. | 600/475 |
| 2008/0119694 A1 * | 5/2008 | Lee | 600/127 |
| 2008/0154257 A1 * | 6/2008 | Sharareh et al. | 606/41 |
| 2009/0005768 A1 * | 1/2009 | Sharareh et al. | 606/17 |
| 2009/0005773 A1 * | 1/2009 | Beeckler et al. | 606/41 |

FOREIGN PATENT DOCUMENTS

| | | |
|---|---|---|
| WO | WO 95/02995 | 2/1995 |
| WO | WO 2007/127228 A2 | 11/2007 |
| WO | WO 2007/146995 A1 | 12/2007 |

OTHER PUBLICATIONS

U.S. Appl. No. 11/281,853, filed Nov. 17, 2005, Sharareh et al.

International Search Report of the International Searching Authority, International Application No. PCT/US2007/071107, mailed Nov. 19, 2007, 5 pgs.

Extended European Search Report dated Jun. 16, 2010 for EP Patent Application No. 10075155.1 (3 pages).

* cited by examiner

FIG. 12A
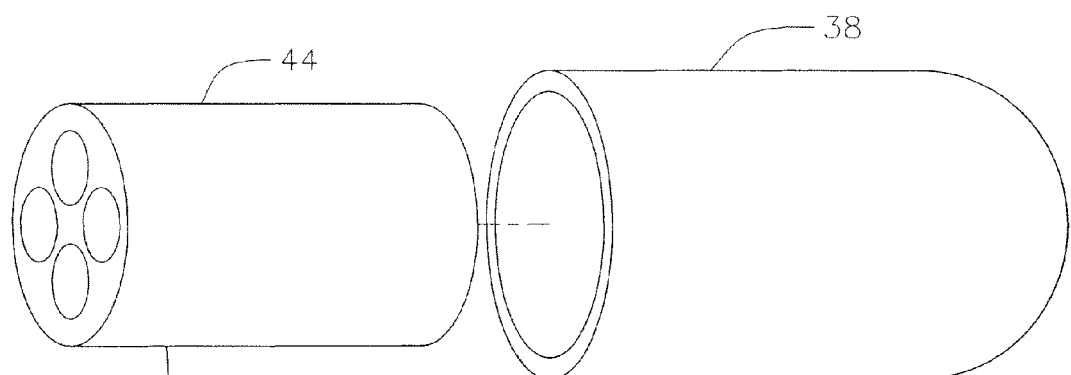
FIG. 12B
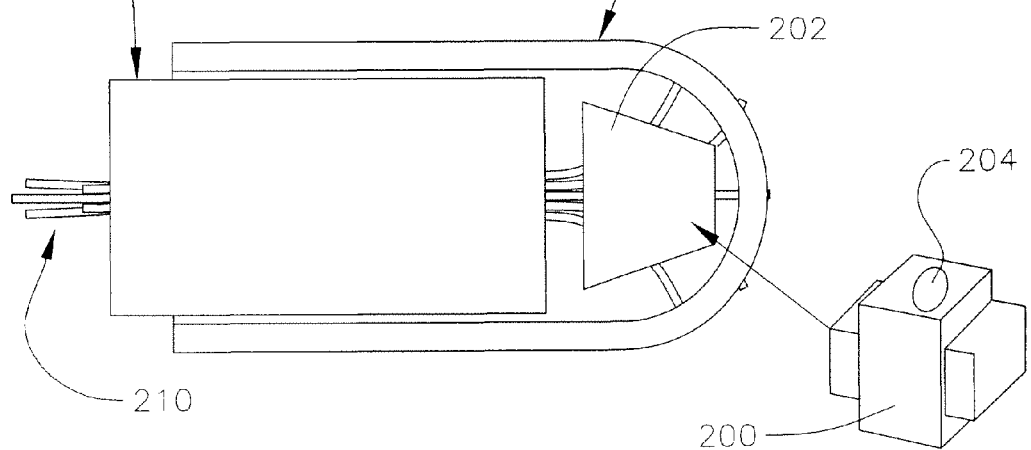
FIG. 12C

CATHETER WITH OMNI-DIRECTIONAL OPTICAL TIP HAVING ISOLATED OPTICAL PATHS

FIELD OF INVENTION

The present invention relates to ablation catheters, and in particular to ablation catheters with optical monitoring of tissue.

BACKGROUND OF THE INVENTION

For certain types of minimally invasive medical procedures, real time information regarding the condition of the treatment site within the body is unavailable. This lack of information inhibits the clinician when employing catheter to perform a procedure. An example of such procedures is tumor and disease treatment in the liver and prostate. Yet another example of such a procedure is surgical ablation used to treat atrial fibrillation. This condition in the heart causes abnormal electrical signals, known as cardiac arrhythmias, to be generated in the endocardial tissue resulting in irregular beating of the heart.

The most frequent cause of cardiac arrhythmias is an abnormal routing of electricity through the cardiac tissue. In general, most arrhythmias are treated by ablating suspected centers of this electrical misfiring, thereby causing these centers to become inactive. Successful treatment, then, depends on the location of the ablation within the heart as well as the lesion itself. For example, when treating atrial fibrillation, an ablation catheter is maneuvered into the right or left atrium where it is used to create ablation lesions in the heart. These lesions are intended to stop the irregular beating of the heart by creating non-conductive barriers between regions of the atria that halt passage through the heart of the abnormal electrical activity.

The lesion should be created such that electrical conductivity is halted in the localized region (transmurality), but care should be taken to prevent ablating adjacent tissues. Furthermore, the ablation process can also cause undesirable charring of the tissue and localized coagulation, and can evaporate water in the blood and tissue leading to steam pops.

Currently, lesions are evaluated following the ablation procedure, by positioning a mapping catheter in the heart where it is used to measure the electrical activity within the atria. This permits the physician to evaluate the newly formed lesions and determine whether they will function to halt conductivity. It if is determined that the lesions were not adequately formed, then additional lesions can be created to further form a line of block against passage of abnormal currents. Clearly, post ablation evaluation is undesirable since correction requires additional medical procedures. Thus, it would be more desirable to evaluate the lesion as it is being formed in the tissue.

A known method for evaluating lesions as they are formed is to measure electrical impedance. Biochemical differences between ablated and normal tissue can result in changes in electrical impedance between the tissue types. Although impedance is routinely monitored during electrophysiologic therapy, it is not directly related to lesion formation. Measuring impedance merely provides data as to the location of the tissue lesion but does not give qualitative data to evaluate the effectiveness of the lesion.

Another approach is to measure the electrical conductance between two points of tissue. This process, known as lesion pacing, can also determine the effectiveness of lesion therapy. This technique, however, measures the success or lack thereof from each lesion, and yields no real-time information about the lesion formation.

Thus, there is a need for a catheter capable of measuring lesion formation in real-time, if not monitoring tissue in general. Because a catheter may assume various orientation angles at the ablation site, there is a further need for a catheter that is capable of such measuring and detecting whether the catheter is parallel, perpendicular or at an angle to the tissue. Moreover, where such measuring and detecting are accomplished through optical spectroscopy, there is a need for a catheter that can provide separate optical paths for light illuminating the tissue and for light recaptured from the tissue.

SUMMARY OF THE INVENTION

The present invention is directed to a catheter that enables real-time light measurements, for example, without limitation, diffuse reflectance, fluorescence, etc., from biological materials, such as tissue (including blood), while performing RF ablation. The catheter tip design isolates illumination and collection paths such that light exits the catheter tip and travels through the tissue of interest (e.g., cardiac tissue or blood) before returning to the catheter tip. Such a design advantageously avoids specular reflection and saturation of the optical detector, and ensures diffusion of the illumination light within the medium of interest.

The light recaptured by the catheter from the tissue conveys tissue parameters that can be evaluated using spectroscopic methods. These parameters include, without limitation, lesion formation, depth of penetration of lesion, and cross-sectional area of lesion, formation of char during ablation, recognition of char during ablation, recognition of char from non-charred tissue, formation of coagulum around the ablation site, differentiation of coagulated from non-coagulated blood, differentiation of ablated from healthy tissue, tissue proximity, evaluation of tissue health, status, and disease state, and recognition of steam formation in the tissue for prevention of steam pop.

In accordance with the present invention, the catheter has a catheter body and a tip section adapted for ablating tissue, the tip section providing separate optical paths for light illuminating the tissue and light recaptured from the tissue. In one embodiment, a tip electrode has a shell defining a hollow cavity, where the shell has in its wall illumination openings to pass light onto the tissue and collection openings to recapture light from the tissue in the hollow cavity. The optical path for light illuminating the tissue includes passage through an optically diffuse material in the tip section and through the illumination openings. The optical path for light recaptured from the tissue includes passage through the collection openings and collection in the hollow cavity. An opaque coating lining the hollow cavity separates the optically diffuse material and the hollow cavity and therefore the two optical paths from each other. Moreover, the catheter may be adapted with irrigation for flushing the collection openings with fluid, such as saline or other biocompatible fluid. Fiber optic cable(s) extend into the tip section to illuminate the optically diffuse material. Other fiber optic cable(s) extend into the tip section to receive the light recaptured in the hollow cavity.

In a more detailed embodiment, a catheter adapted to ablate tissue has a catheter body and a tip electrode adapted for ablating tissue. The tip electrode has an exterior shell, an inner layer of diffuse material and a hollow cavity, wherein the inner layer is configured to transmit light outside the tip electrode to a tissue via illumination openings in the shell wall, and the hollow cavity is configured to receive light from the tissue via collection openings in the shell wall and the inner layer. An inner surface of the inner layer has an opaque coating to isolate light injected into the inner layer from light collected in the hollow cavity. At least one optical waveguide extends between the catheter body and the tip electrode to inject light into the inner layer to provide the tip electrode with light to illuminate the tissue. To that end, the inner layer of diffuse material may have projections that extend into the illumination openings in the shell wall to facilitate transmission of the light to outside the tip electrode. At least another optical waveguide extends between the catheter body and the tip electrode to collect the light from the tissue recaptured in the hollow cavity.

As an omnidirectional illuminator and collector, the tip electrode has a distal portion defining a first section that is generally perpendicular to a longitudinal axis of the tip electrode, a second section that is at an angle between about 30 and 60 degrees with the longitudinal axis, and a third section that is generally parallel with the longitudinal axis. The illumination openings are configured in the second section and in the third section but may also be present in the first section. The collection openings are configured in the first and third sections but may also be present in the second section. The catheter may have a deflectable intermediate section between the catheter body and the tip electrode. It may also carry a temperature sensor and a location sensor in the tip section.

The present invention is also directed to a method of making an ablation tip electrode that also functions as an omnidirectional illuminator and collector. The method includes providing a shell having a wall that defines an open proximal end and a generally dome shape distal end, configuring illumination openings through the shell wall, filling the shell with a moldable or injectable diffuse material, configuring a hollow cavity at the distal end of the shell, and configuring collection openings through the shell wall and the moldable diffuse material and into the hollow cavity. The method includes providing an optical barrier between the moldable plastic material and the hollow cavity, inserting a fiber optic cable into the moldable diffuse material to provide light to the tip electrode, and inserting a fiber optic cable into the hollow cavity to receive recaptured light in the hollow cavity.

The method further includes providing a plug to seal the hollow cavity, and configuring the plug with passages for the fiber optic cables. The portions of the fiber optic cables in the passages may be fixedly secured within the passages by glue, adhesive or the like, to stabilize the fiber optic cables and reduce the risk of breakage or detachment.

The present catheter and method are designed to use light in conjunction with irrigation and the technology of RF ablation. Advantageously, the light used to monitor and assess the tissue (or a lesion formed in the tissue) is generally not affected by the portion of the electromagnetic radiation used for ablation. Moreover, the bandwidth used for monitoring and assessing also transmits through blood with minimal attenuations. The fiber optics are used and disposed in the catheter in a manner that avoids contact with tissue, which can increase the operative lifetime of the catheter and minimize damages caused by abrasion to the fiber optics. Furthermore, the alignment plug in the tip electrode secures the fiber optic cables with minimal bend or strain but increased angular coverage, which can minimize fiber optics breakage during assembly and use, as well as reduce nonlinear optical effects caused by orientation of the fiber optics. In addition, the use of fiber optics to emit and receive light is a generally temperature neutral process that adds little if any measurable heat to surrounding blood or tissue.

BRIEF DESCRIPTION OF THE DRAWINGS

These and other features and advantages of the present invention will be better understood by reference to the following detailed description when considered in conjunction with the accompanying drawings wherein:

FIG. 12*a* is an exploded side elevational view of an embodiment of a tip electrode and a plug.

FIG. 12*b* is a cross sectional view of an embodiment of an assembled tip electrode with a plug and an internal fixture member.

FIG. 12*c* is a perspective view of an embodiment of an internal fixture member.

DETAILED DESCRIPTION OF THE INVENTION

Figure 1:
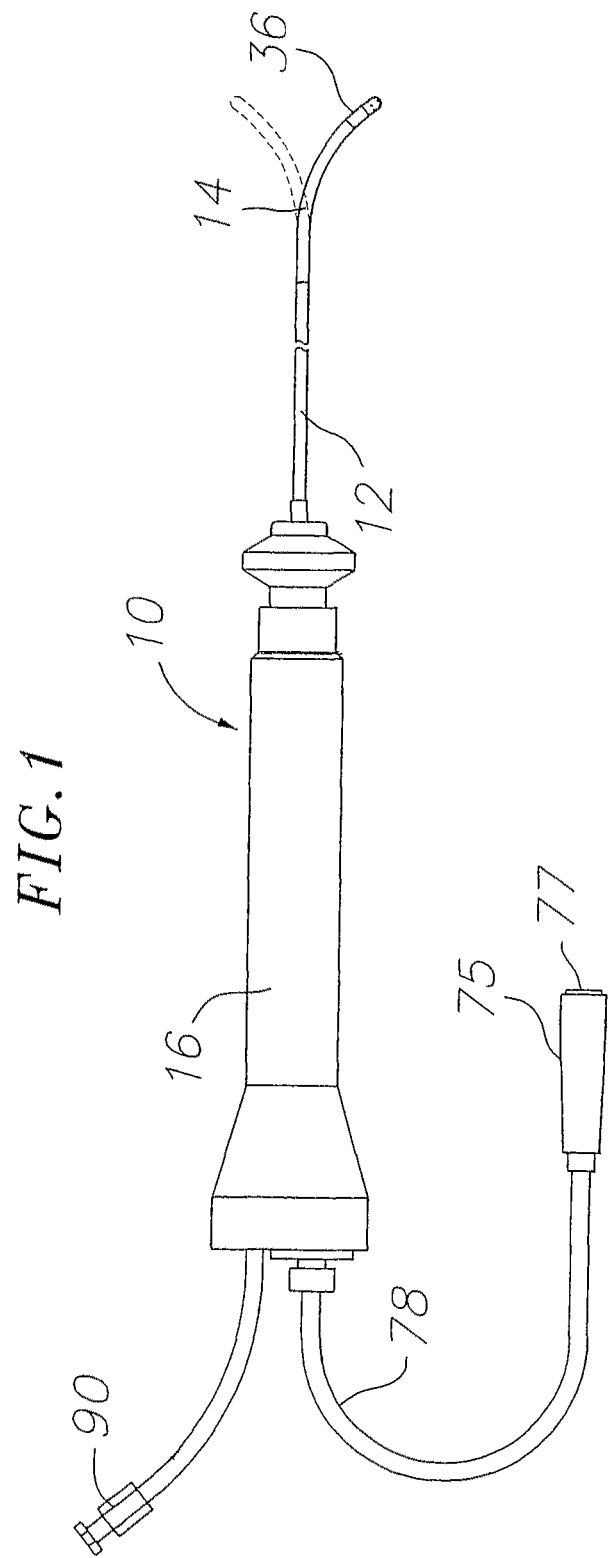
FIG. 1 is a side view of an embodiment of the catheter of the present invention.

As shown in FIGS. 1-11, catheter 10 of the present invention comprises an elongated catheter body 12 having proximal and distal ends, a deflectable (uni- or bi-directionally) intermediate section 14 at the distal end of the catheter body 12, a tip section 36 at the distal end of the intermediate section, and a control handle 16 at the proximal end of the catheter body 12.

Figure 2A:
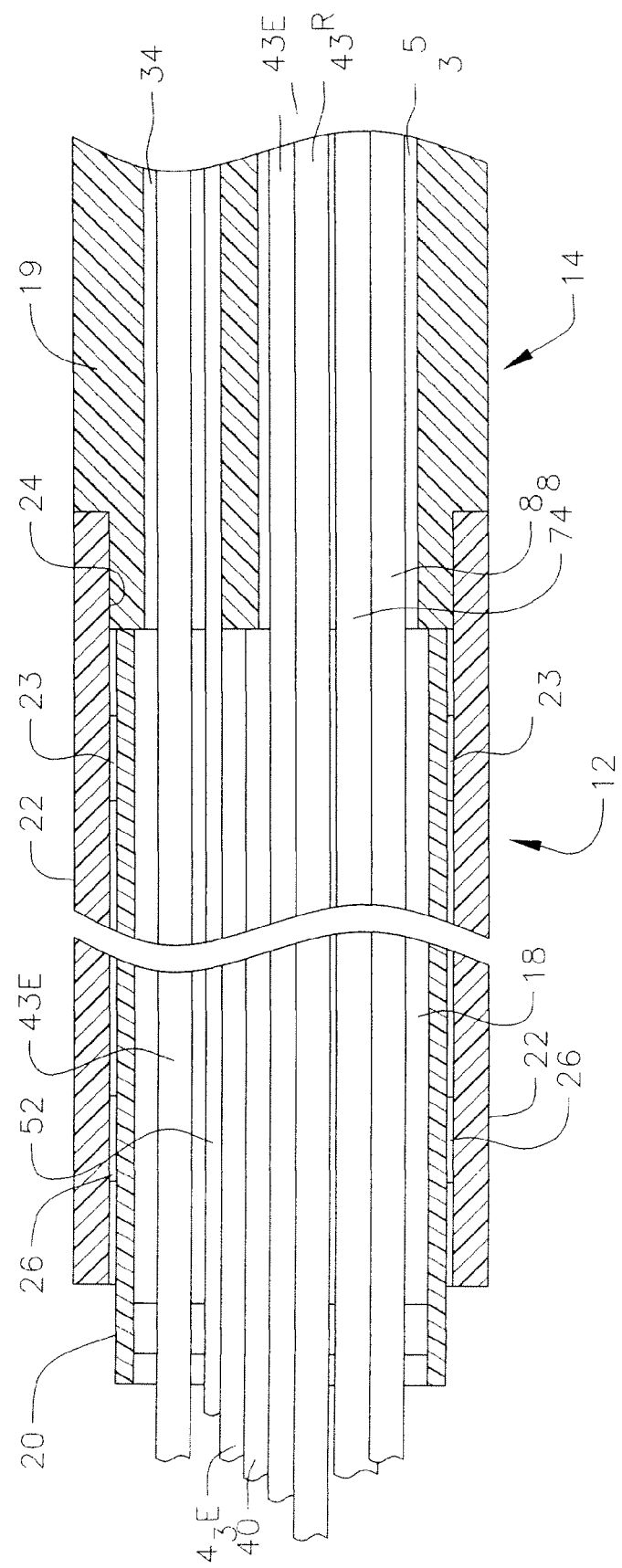
FIG. 2A is a side cross-sectional view of an embodiment of a catheter according to the invention, including a junction between a catheter body and an intermediate section, taken along a first diameter.
Figure 2B:
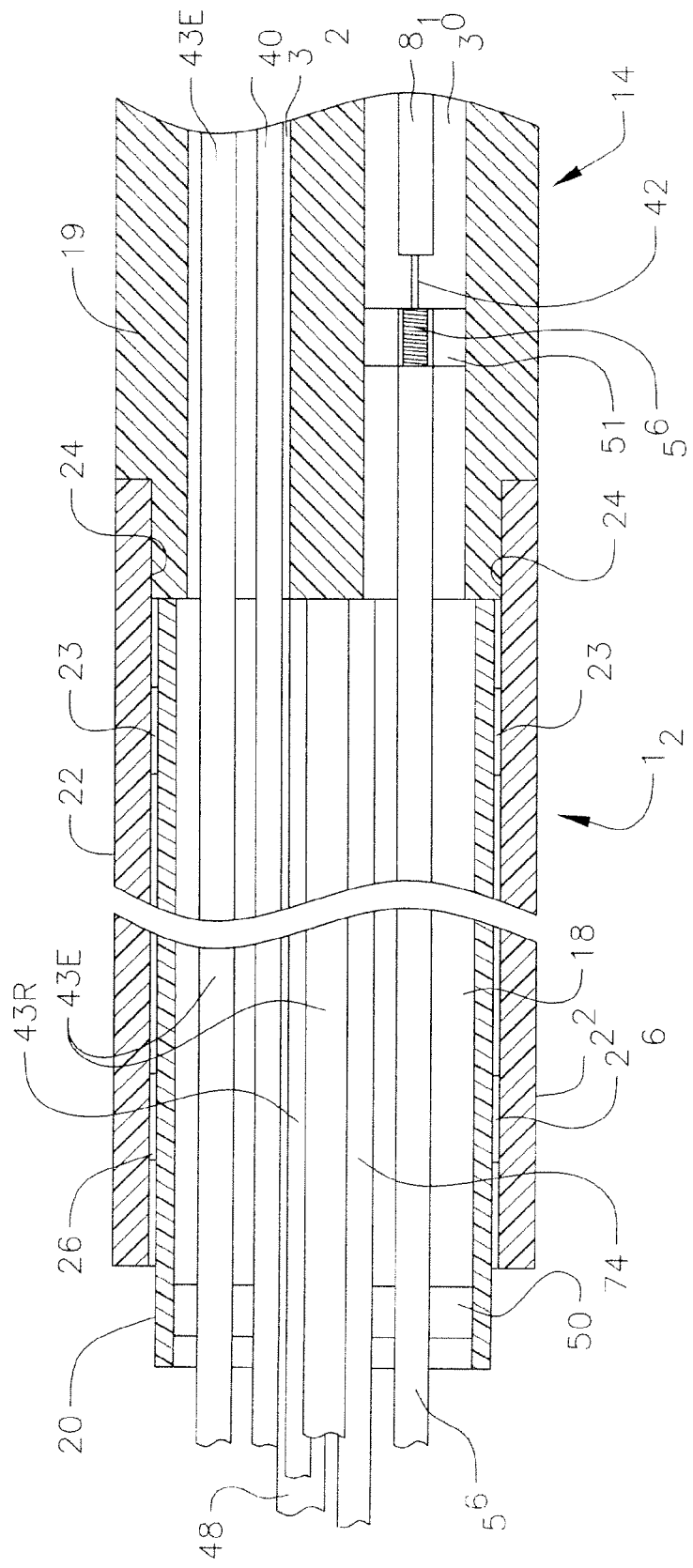
FIG. 2B is a side cross-sectional view of an embodiment of a catheter according to the invention, including the junction between the catheter body and the intermediate section, taken along a second diameter generally perpendicular to the first diameter of FIG. 2A.

With additional reference to FIGS. 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A construction comprises an outer wall 22 made of an extruded plastic. The outer wall 22 may comprise an imbedded braided mesh of stainless steel or the like to increase torsional stiffness of the catheter body 12 so that, when the control handle 16 is rotated, the catheter body 12, the intermediate section 14 and the tip section 36 of the catheter 10 will rotate in a corresponding manner.

Extending through the single lumen 18 of the catheter body 12 are components, for example, lead wire 40 and thermocouple wires 41, 45 protected by a sheath 52, fiber optic cables 43, a first irrigation tube segment 88, a compression coil 56 through which a puller wire 42 extends, and an electromagnetic sensor cable 74. A single lumen catheter body can be preferred over a multi-lumen body because it has been found that the single lumen body permits better tip control when rotating the catheter. The single lumen permits the various components such as the lead wire, thermocouple wires, infusion tube, and the puller wire surrounded by the compression coil to float freely within the catheter body. If such wires, tube and cables were restricted within multiple lumens, they tend to build up energy when the handle is rotated, resulting in the catheter body having a tendency to rotate back if, for example, the handle is released, or if bent around a curve, to flip over, either of which are undesirable performance characteristics.

The outer diameter of the catheter body 12 is not critical, but is preferably no more than about 8 french, more preferably 7 french. Likewise the thickness of the outer wall 22 is not critical, but is thin enough so that the central lumen 18 can accommodate the aforementioned components. The inner surface of the outer wall 22 may be lined with a stiffening tube 20, which can be made of any suitable material, such as polyimide or nylon. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing may be preferred for the stiffening tube 20 because it may be very thin walled while still providing very good stiffness. This maximizes the diameter of the central lumen 18 without sacrificing strength and stiffness.

The catheter may have an outer wall 22 with an outer diameter of from about 0.090 inch to about 0.104 inch and an inner diameter of from about 0.061 inch to about 0.075 inch and a polyimide stiffening tube 20 having an outer diameter of from about 0.060 inch to about 0.074 inch and a wall thickness of about 0.001-0.005 inch.

Figure 3:
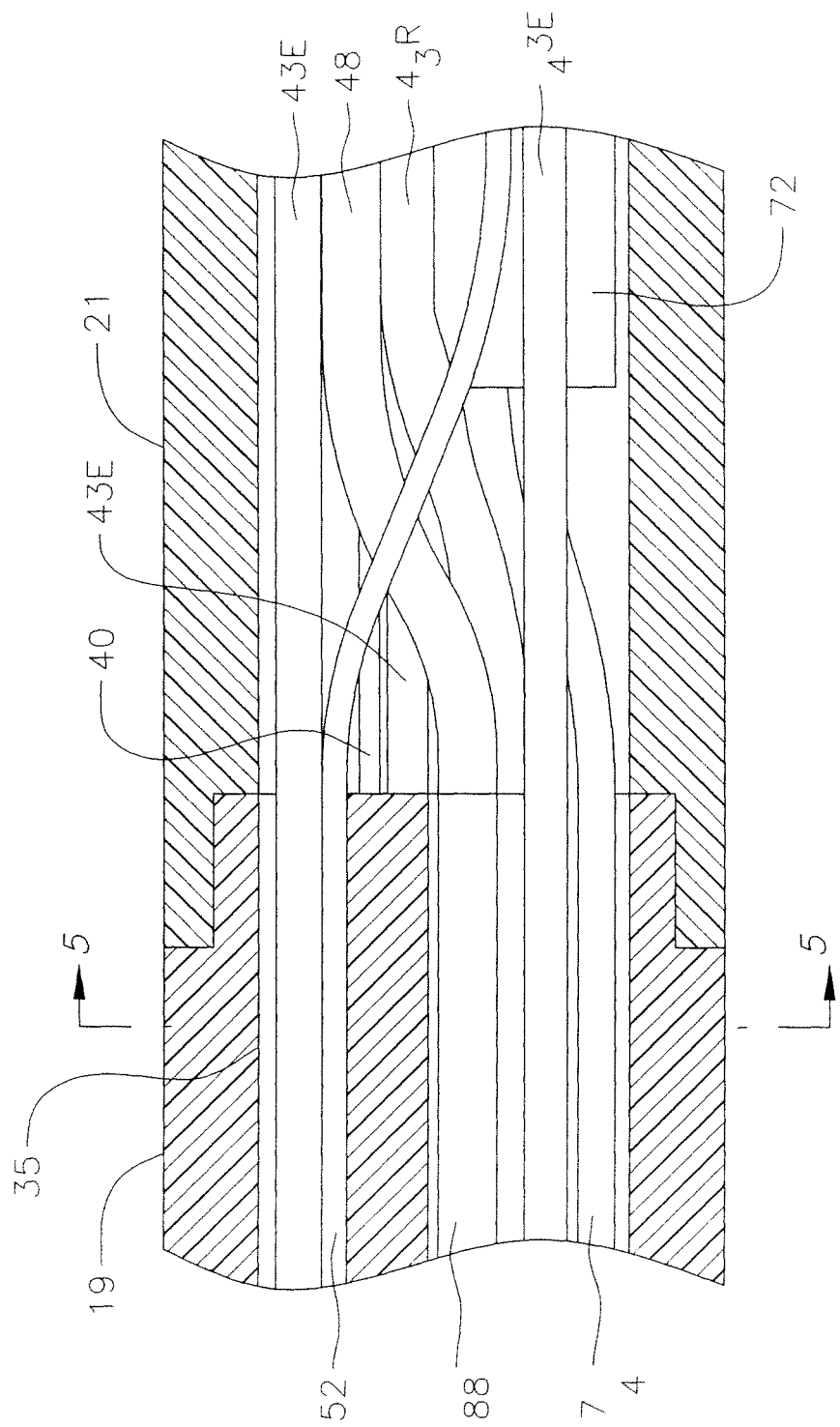
FIG. 3 is a side cross-sectional view of an embodiment of a catheter according to the invention, including a junction between the intermediate section and a tip section, taking along the first diameter.
Figure 5:
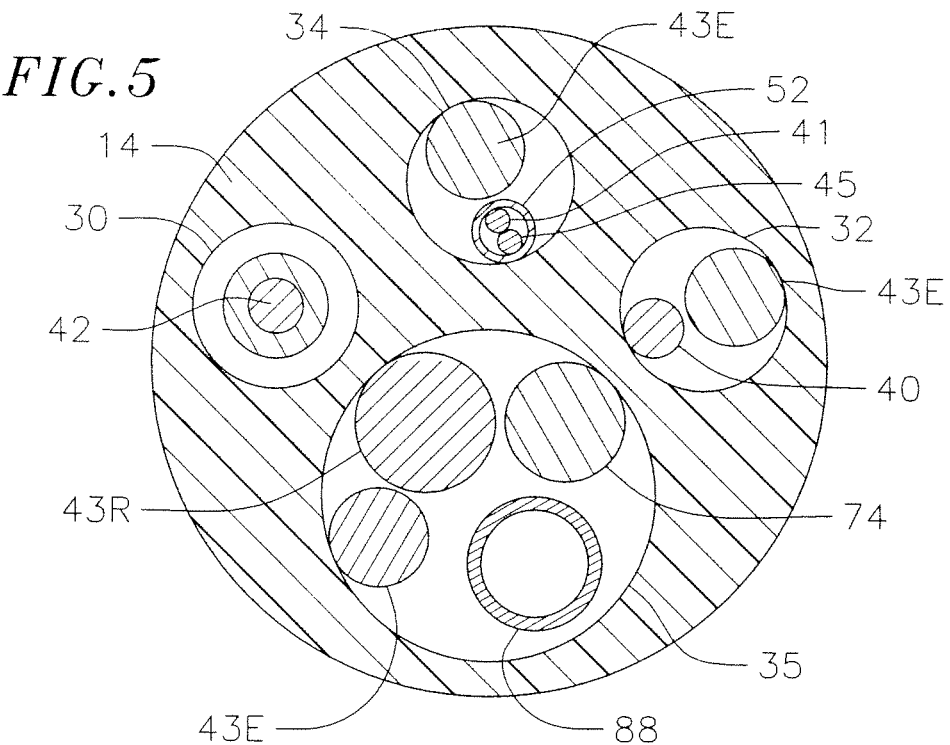
FIG. 5 is a longitudinal cross-sectional view of an embodiment of an intermediate section of FIG. 3, taken along line 5-5.

Referring also to FIGS. 3 and 5, the intermediate section 14 distal of the catheter body 12 comprises a shorter section of tubing 19 having multiple lumens. The tubing 19 is made of a suitable non-toxic material that is preferably more flexible than the catheter body 12. A suitable material for the tubing 19 is polyurethane braded with a low to medium durometer plastic. The outer diameter of the intermediate section 14, like that of the catheter body 12, is preferably no greater than about 8 french, more preferably 7 french. The size and number of the lumens is not critical. In an embodiment, the intermediate section 14 has an outer diameter of about 7 french (0.092 inch). The tubing has a first off-axis lumen 30, a second off-axis lumen 32 and a third off-axis lumen 34 that are generally about the same size, each having a diameter of from about 0.020 inch to about 0.024 inch, preferably 0.022 inch. The tubing also has a fourth off-axis lumen 35 having a larger diameter of from about 0.032 inch to about 0.038 inch, preferably 0.036 inch.

Referring to FIGS. 2A and 2B, the catheter body 12 may be attached to the intermediate section 14 comprises an outer circumferential notch 24 configured in the proximal end of the tubing 19 that receives the inner surface of the outer wall 22 of the catheter body 12. The intermediate section 14 and catheter body 12 are attached by glue or the like. Before the intermediate section 14 and catheter body 12 are attached, the stiffening tube 20 is inserted into the catheter body 12. The distal end of the stiffening tube 20 is fixedly attached near the distal end of the catheter body 12 by forming a glue joint 23 with polyurethane glue or the like. Preferably a small distance, e.g., about 3 mm, is provided between the distal end of the catheter body 12 and the distal end of the stiffening tube 20 to permit room for the catheter body 12 to receive the notch 24 of the intermediate section 14. If no compression coil is used, a force is applied to the proximal end of the stiffening tube 20, and, while the stiffening tube 20 is under compression, a first glue joint (not shown) is made between the stiffening tube 20 and the outer wall 22 by a fast drying glue, e.g. cyanoacrylate. Thereafter a second glue joint 26 is formed between the proximal ends of the stiffening tube 20 and outer wall 22 using a slower drying but stronger glue, e.g., polyurethane.

If desired, a spacer can be located within the catheter body between the distal end of the stiffening tube and the proximal end of the tip section. The spacer provides a transition in flexibility at the junction of the catheter body and intermediate section, which allows this junction to bend smoothly without folding or kinking. A catheter having such a spacer is described in U.S. patent application Ser. No. 08/924,616, entitled "Steerable Direct Myocardial Revascularization Catheter", the entire disclosure of which is incorporated herein by reference.

Figure 4A:
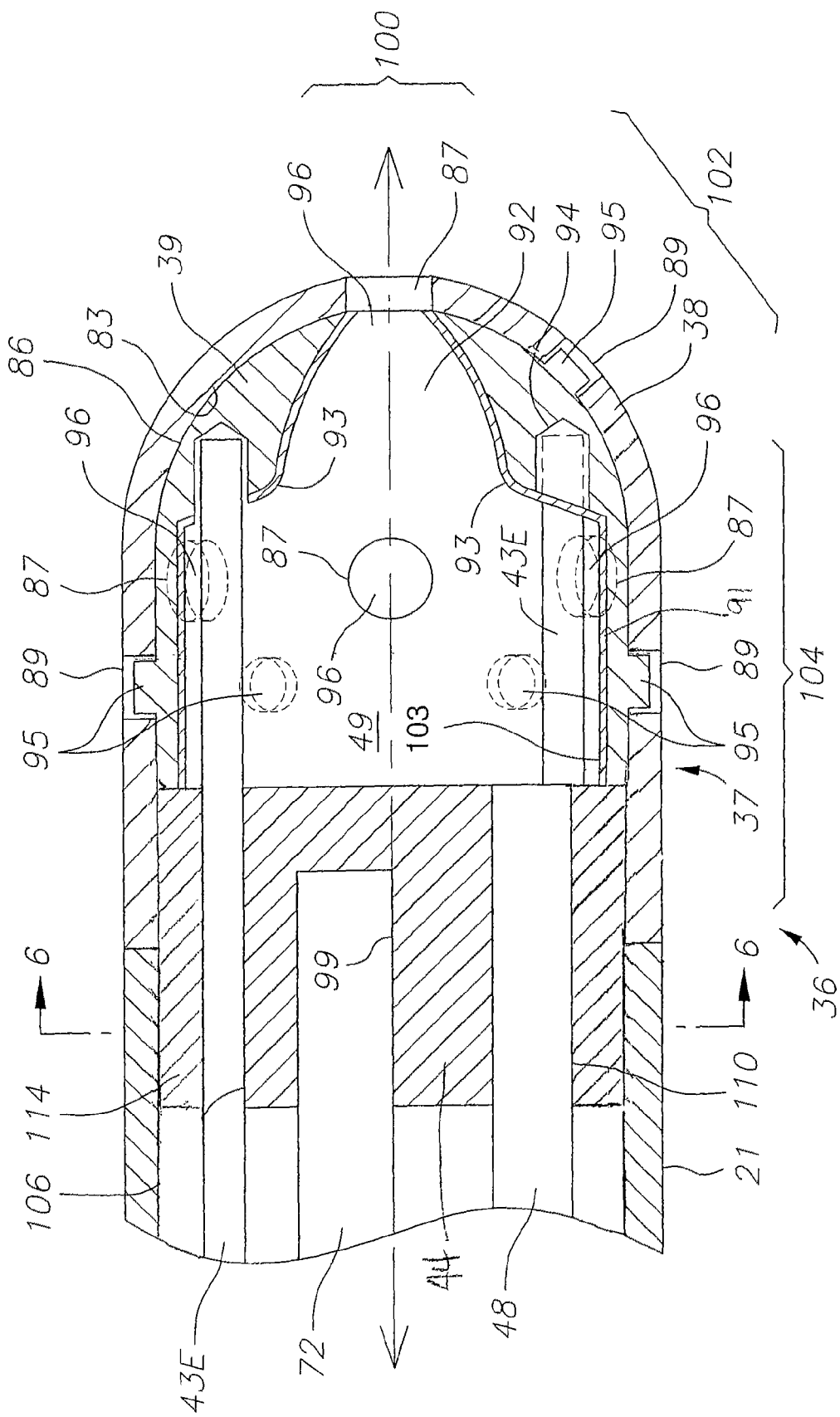
FIG. 4A is a side cross sectional view of an embodiment of a catheter according to the invention, including a junction between a plastic housing and a tip electrode, taken along the first diameter.
Figure 4B:
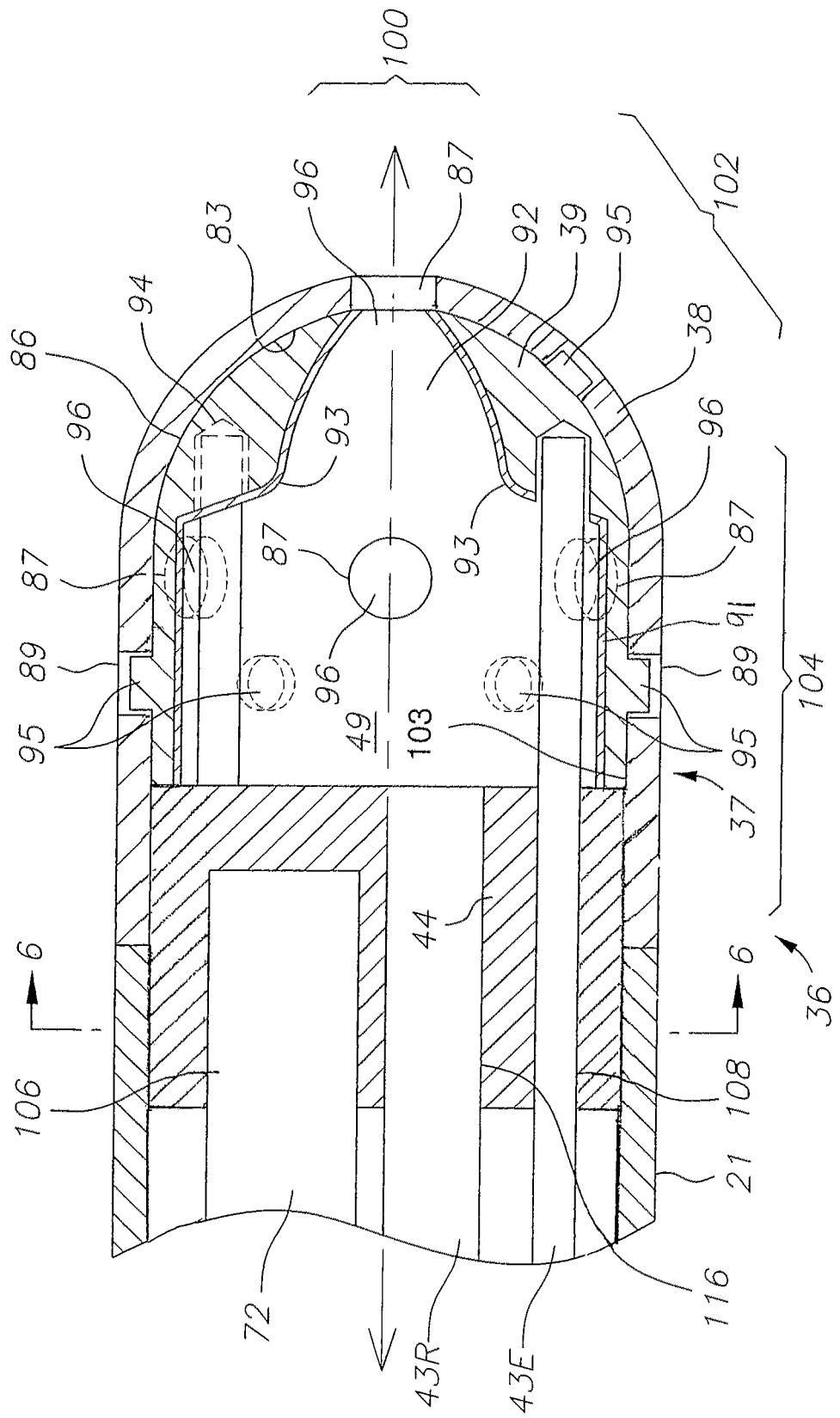
FIG. 4B is a side cross-sectional view of an embodiment of a catheter according to the invention, including a junction between a plastic housing and a tip electrode, taken along the second diameter generally perpendicular to the first diameter of FIG. 4A.

Extending from the distal end of the intermediate section 14 is the tip section 36 that includes a tip electrode 37 and a plastic housing 21 as shown in FIGS. 4A and 4B. The plastic housing 21 connects the tip electrode 37 and the tubing 19 and provides components that extend through its lumen with housing and/or transitional space, as discussed further below. The plastic housing 21 is preferably made of polyetheretherketone (PEEK) and may be about 1 cm long. Its proximal end comprises an inner circumferential notch 27 (FIG. 3) that receives an outer circumferential notch surface of the tubing 19 of the intermediate section 14. The intermediate section 14 and the plastic housing 21 are attached by glue or the like. Components such as wires, cables and tube segments that extend between the intermediate section 14 and the tip electrode 38 help keep the tip electrode in place.

The tip electrode 37 has an open proximal end that is in communication with a generally hollow distal portion or cavity 49, and is of a three-piece construction. The tip electrode comprises an outer shell 38 (FIG. 7) having a wall of generally uniform thickness, an inner layer 39 (FIG. 8) and a press-fit plug or alignment member 44 (FIG. 6) positioned at or near the proximal end of the shell.

Figure 7:
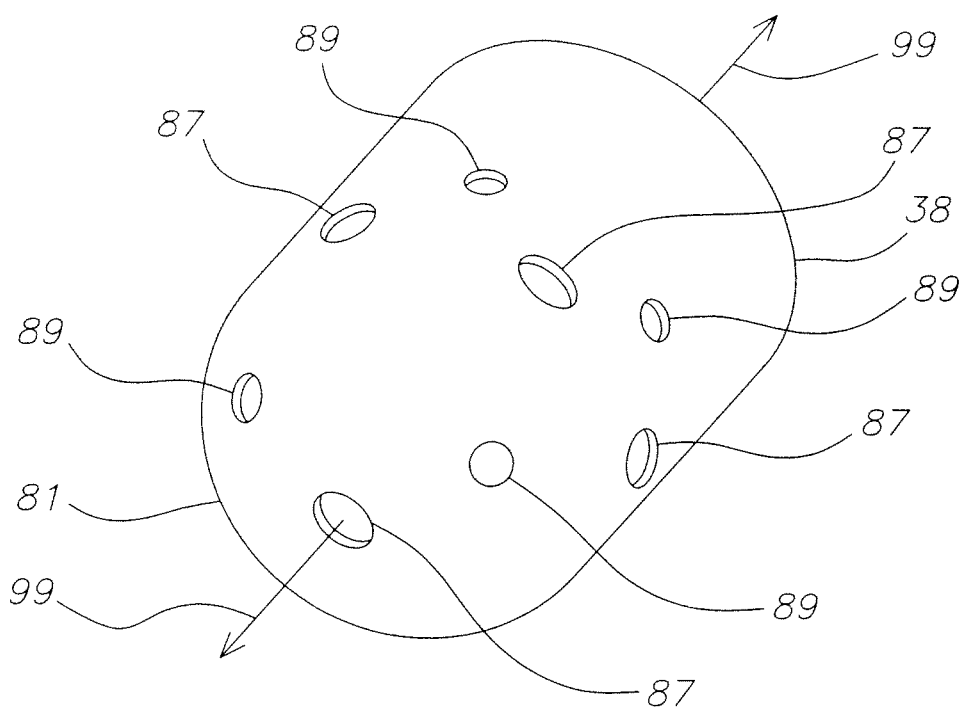
FIG. 7 is a perspective view of an embodiment of a shell of the tip electrode.

With reference to FIG. 7, the shell 38 is configured with a dome or similar shape at its distal end to facilitate omnidirectional illumination and collection of light. Its exterior 81 is atraumatic, smooth without significant protrusions, and adapted for contact with tissue. The shell wall is configured with a plurality of through-holes or openings of various sizes, including collection openings 87 and illumination openings 89, at predetermined locations on the shell 38. The shell is formed from any suitable material that is both thermally and electrically conductive which allows for radio frequency ablation using an RF generator. Such suitable materials include, without limitation, platinum-irridium, platinum, gold alloy, or palladium alloy.

Figure 9:
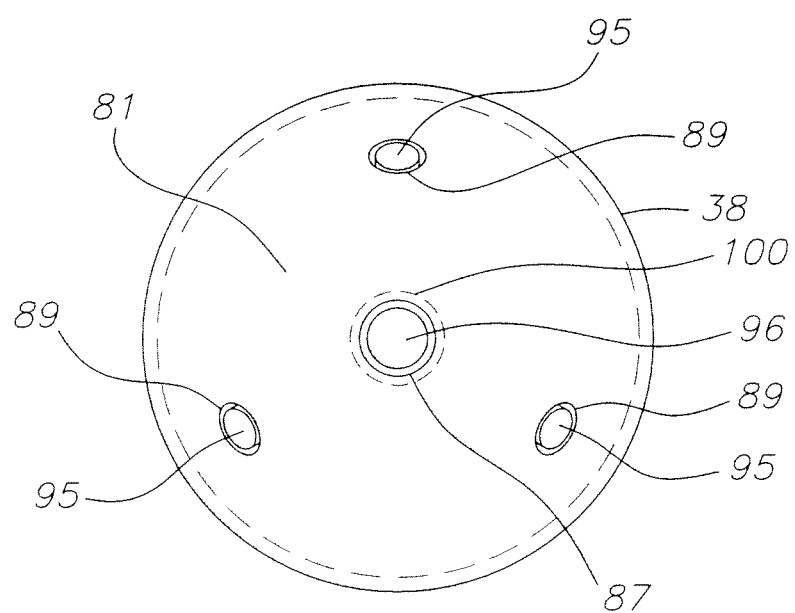
FIG. 9 is a front end view of an embodiment of a tip electrode.
Figure 8:
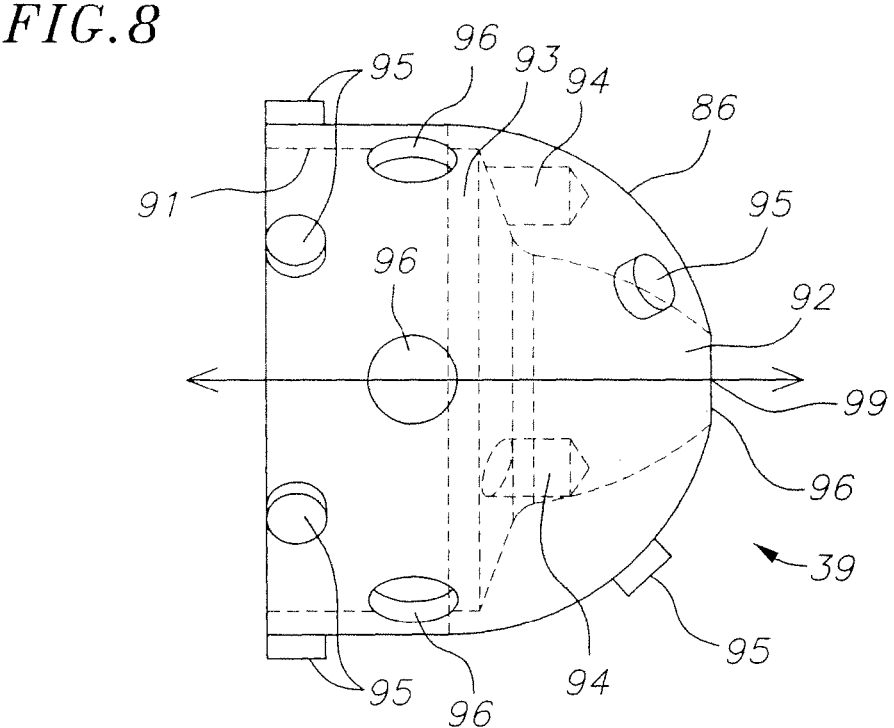
FIG. 8 is a side elevational view of an embodiment of an inner layer of the tip electrode.
Figure 10:
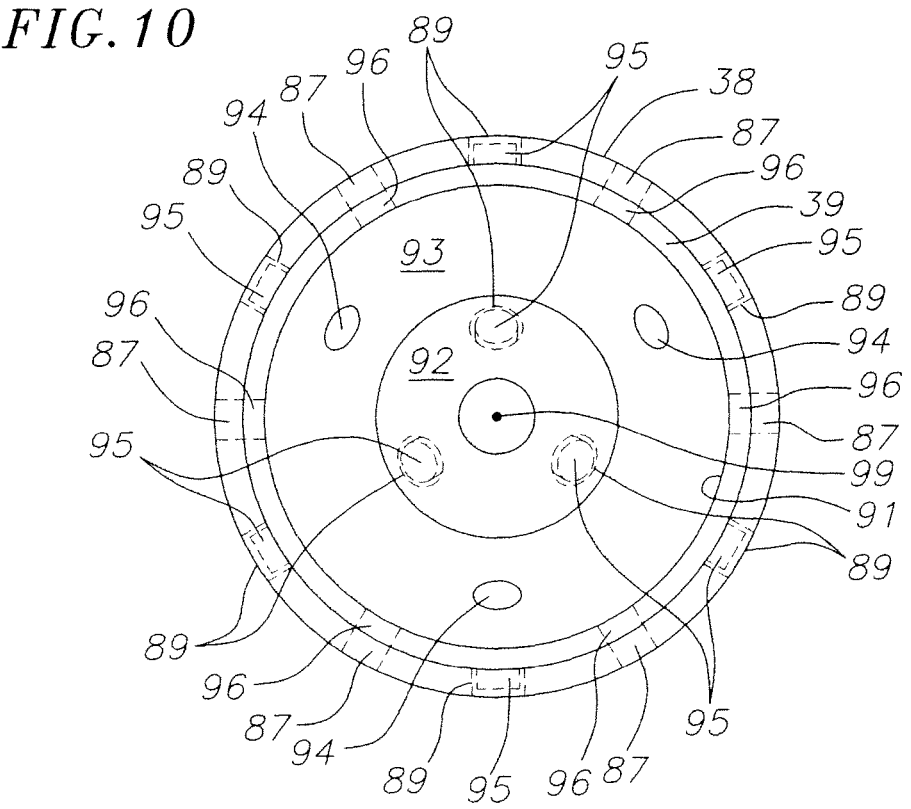
FIG. 10 is an end view of the tip electrode of FIG. 9.

With reference to FIG. 8, the inner layer 39 is an injection-moldable optically transmissive plastic material compounded with optical scattering material, for example, Teflon powder or barium sulfate ($BaSO_4$) powder, into which light can be injected for diffusion throughout the inner layer. A material is suitable provided it is biocompatible and optically diffusive. As shown in FIGS. 9 and 10, the inner layer 39 is configured (i) to receive light and (ii) to diffuse the light into multiple directions and deliver the light to outside the tip electrode through each illumination opening 89 in the shell wall. In the first instance, a plurality of recesses 94 are provided to receive fiber optic cables that inject light into and illuminate the inner layer 39. In the second instance, outer surface 86 of the inner layer 39 is configured in general conformity with the inner surface of the shell 38, and at locations corresponding to the openings 89 in the shell wall projections or extrusions 95 on the outer surface 86 extend into the openings 89 so that light within the inner layer 39 is diffusely transmitted to the openings 89 and to outside the tip electrode.

The inner layer 39 is also configured to minimize obstruction to the optical collecting function of the tip electrode. To that end, the collection openings 87 of the shell wall extend through the inner layer 39 so there is communication between outside the tip electrode and the hollow cavity 49. Moreover, the inner surface 91 can provide a rim region 93 that circumscribes a generally conical/parabolic distal portion 92 of the hollow cavity 49 which optimizes diffusion of light injected into the inner layer 39 and optimizes the amount of light received in the hollow cavity 49 from outside the tip electrode 37.

The hollow cavity 49 is physically and optically separated from the inner layer 39 by a an opaque barrier. In the disclosed embodiment, the hollow cavity 49 is defined by inner surface 91 of the inner layer 39 which is coated with a layer of opaque material 103, for example, gold, to keep light in the inner layer 39 from entering the hollow cavity 49 (and vice versa).

Figure 11A:
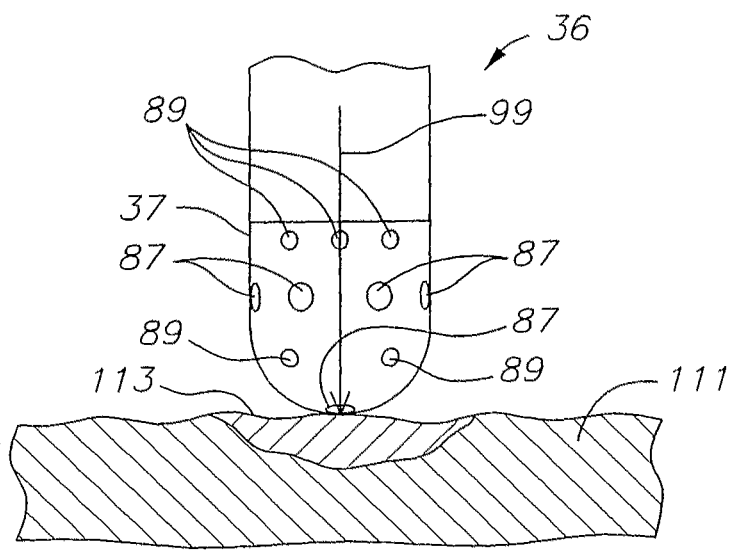
FIG. 11A is a side view of an embodiment of a tip section whose longitudinal axis is generally perpendicular to tissue surface.
Figure 11B:
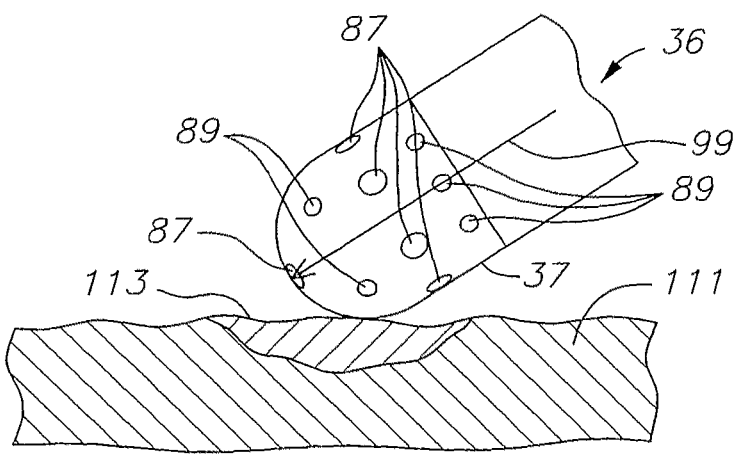
FIG. 11B is a side view of an embodiment of a tip section whose longitudinal axis is generally at an angle between zero and 90 to tissue surface.
Figure 11C:
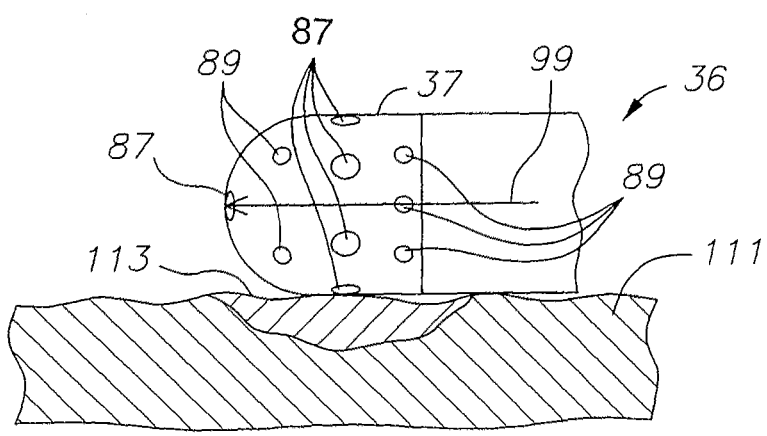
FIG. 11C is a side view of an embodiment of a tip section whose longitudinal axis is generally parallel to tissue surface.

In accordance with the invention, the tip electrode 37 has multiple sections relative to its longitudinal axis 99, as shown in FIGS. 4A and 4B, in rendering the tip omnidirectional for optical tissue monitoring. In the illustrated embodiment, there are a distal section 100, a mid-section 102 and a proximal section 104. The distal section 100 is generally perpendicular to the axis. The mid-section 102 is generally at an angle ranging between zero and 90 degrees, preferably about 30 to 60 and more preferably about 45 degrees to the axis. The proximal section 104 is generally parallel with the axis. These differently-angled sections enable the tip electrode 37 to operate as an illuminator and a collector for various angles between the tip section 36 and the tissue as shown in FIGS. 11A-11C.

Each section can have any number of illumination and/or collection openings as desired or appropriate. In the illustrated embodiment, the distal section 100 has a collection opening 87 at the distal end of the tip electrode along its longitudinal axis 99. The mid-section 102 has three illumination openings 89 that are equi-angular from each other at about 120 degrees about the axis. The proximal section 104 has six more collection openings 87 that are equi-angular from each other at about 60 degrees about the axis. Three alternating of these six collection openings 87 are generally in radial alignment with the three recesses 94 in the rim section 93 and the other three alternating are generally in radial alignment with the illumination openings 89 in the mid-section 102. Also in the proximal section 104 proximal the collection openings 87 are another six illumination openings 89 that are equi-angular from each other at about 60 degrees about the axis. These illumination openings 89 are offset from the six collection openings 87 in the proximal section 104.

Figure 6:
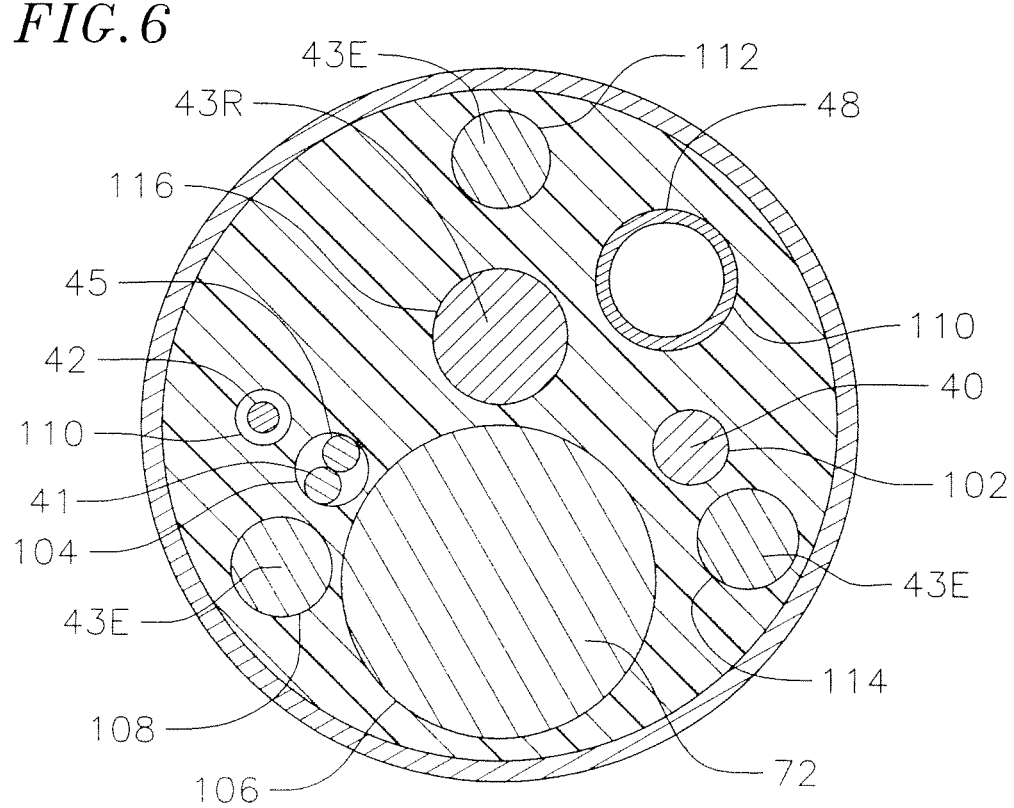
FIG. 6 is a longitudinal cross-sectional view of an embodiment of a plastic housing of FIGS. 4A and 4B, taken along line 6-6.

Formed of the same or comparable material as the shell 38, the plug 44 has a generally elongated cylindrical configuration having a predetermined length and a generally circular cross-section. A distal portion of the plug 44 is press fitted into the open proximal end of the tip electrode 37 to seal the hollow cavity 49, while a proximal portion of the plug 44 extends proximally from the tip electrode 37 for attachment to the housing 21. The distal portion of the plug 44 may also be slip fitted and sealed with solder. As shown in FIG. 6, various blind holes and passages are provided in the plug to allow components to be anchored to the plug or to pass through to the hollow cavity 49. In the illustrated embodiment, there are blind holes 101, 102, 104 and 106 in which distal ends of the puller wire 42, the lead wire 40, the pair of thermocouple wires 41 and 45 and the location sensor 72 are anchored, respectively. There are also passages 108, 112, 114, and 116 through which the fiber optic cables 43 extend, and a passage 110 through which an irrigation tube segment 48 extends. The blind hole 101 for anchoring the distal end of the puller wire is generally aligned with the lumen 30 of the tubing 19 of the intermediate section 14. (The distal end of the puller wire can also be anchored in the side wall of tubing 19 at the distal end of the intermediate section 14.) The passages 108, 112 and 114 for three fiber optic cables 43 are generally aligned with the recesses 94 in the rim section 93 of the inner layer 39 of the tip electrode. The portions of the components extending through the passages in the plug are securely fixed in the passages by glue, adhesive or the like. As such, the passages help align, stabilize and secure the various components extending through the plug 44.

In accordance with a feature of the present invention, the catheter 10 is adapted to facilitate optically-based real-time assessment of ablation tissue characteristics, including without limitation, lesion formation, depth of penetration of the lesion, cross-sectional area of the lesion, formation of char during ablation, recognition of char during ablation, differentiation of char from non-charred tissue, formation of coagulum around the ablation site, differentiation of coagulated from non-coagulated blood, differentiation of ablated from healthy tissue, tissue proximity, and recognition of steam formation in the tissue for prevention of steam pop. These assessments are accomplished by measuring the light intensity at one or more wavelengths that is recaptured at the catheter resulting from the light radiated from the catheter tip onto ablated tissue. In that regard, the catheter has fiber optic cables 43 extending into the tip electrode 37 to transmit light to the tip electrode and to collect light recaptured from the tissue.

The fiber optic cables 43 are protectively housed in the catheter from the control handle 16 to the tip section 36. As shown in FIGS. 2B and 5, they extend through the central lumen 18 of the catheter 12 and the lumens 32, 34 and 35 of the intermediate section 14. They extend through the plastic housing 21 and into the tip electrode 37 via the passages 108, 112, 114 and 116 in the plug 44. The passages help minimize stress on the cables 43E and 43R in their transition between the intermediate section 14 and the tip electrode 37. In particular, with the portions of the cables extending through the passages being fixedly secured by glue, adhesive or the like to the passages, the distal portions of the cables should also remain fixed relative to the inner layer 39.

In the disclosed embodiment, there are three cables 43E and one cable 43R. The cables 43E function as a light emitters by transmitting light to the tip electrode 37 from a remote light source. The cable 43R functions as a light receiver by collecting light from the hollow cavity 49 in the tip electrode 37. It is understood by one of ordinary skill in the art that optical waveguides and fiber optic cables in general serve to transmit optical energy from one end to the other, although these are not exclusive.

The emitting fiber optic cables 43E have their distal ends received and fixed in the recesses 94 of the inner layer 39. As such, light from the cables is injected into the inner layer 39 which diffuses the light throughout the inner layer 39, including the projections 95 which in turn transmit light out the openings 89 of the tip electrode 37 and onto tissue of interest 111, as shown in FIGS. 11A-11C.

As lesion 113 forms in the tissue 111 from ablation carried out by tip electrode 37 of the catheter 10 (or by another catheter), its characteristics are altered as understood by one of ordinary skill in the art. In particular, as the lesion is radiated by light, the light is scattered and/or reflected back toward the tip electrode 37, where such light having interacted or otherwise having been affected by the lesion bears qualitative and quantitative information about the lesion 113 as it is recaptured by the hollow cavity 49 via the collection openings 87 of the tip electrode.

Within the hollow cavity 49, the opaque coating 103 lining the inner surface 91 of the inner layer 39 prevents the light from entering the inner layer 39. With its distal end inserted into the hollow cavity, the receiving fiber optic cable 43R collects the recaptured light which bears the qualitative and quantitative information and is transmitted to an optical processing system, as described below in further detail. The conical distal portion 92 of the hollow cavity 49 helps direct light entering the hollow cavity from the distal end of the tip electrode and optimizes the collection of light by the fiber optic cable 43R.

In accordance with the present invention, the tip electrode 37 provides separate optical paths for the light that illuminates tissue and the light recaptured from the tissue. The optical path from the tip electrode to the tissue begins with light that is injected into the inner layer 39 which is diffusely scattered throughout the layer 39 into multiple angles and directions and into the projections 95 that extend into the illumination openings 89 of the tip electrode 37. Exiting the tip electrode 37 from the illumination openings 89, the light is incidental on the tissue of interest, interacts with the tissue and is reflected or scattered back to the tip electrode from the tissue. The separate optical path from the tissue back to the tip electrode begins with entry through the collection openings 87 and then collection in the hollow cavity 49. The optical barrier in the form of the opaque coating 103 between the inner layer 39 and the hollow cavity 49 helps avoid saturation of the fiber optic cable 43R, and to ensure diffusion of the illumination light within the tissue.

As described earlier, the variously-angled sections 100, 102 and 104 of the tip electrode 37 enables radiation and collection of lesion optical data at a variety of angles between the tip electrode and the tissue surface. Each emission and collection openings 89 and 87 in the shell 38 defines an optical cone of radiation, the combinations of which envelope the tip electrode. Accordingly, illumination and recapture of light by the fiber optic cables are possible for a most angles between the tissue and the tip electrode. In accordance with a feature of the present invention, the tip section 36 serves as a generally omni-directional optical radiator and collector. The tip electrode may assume a nearly perpendicular angle with the tissue surface (FIG. 11A), a nearly parallel angle (FIG. 11C) or any angle between about zero and 90 degrees (FIG. 11B). It is understood by one of ordinary skill in the art that the plurality and configuration of the sections 100, 102 and 104 and of the collection and illumination openings may be varied as appropriate or desired. The size and dimensions of each section may also be varied as appropriate or desired, as well as the shape of the openings, which can be round, ovular, square, polygonal, flat(slit), or any combination of these shapes.

It is understood that the fiber optic cables 43E and 43R may be any suitable optical wave guide wherein light introduced at one of the cable is guided to the other end of the cable with minimal loss. Each of the cables 43E and 43R may be a single fiber optic cable or fiber bundles. They may be single mode (also known as mono-mode or uni-mode), multi-mode (with step index or graded index) or plastic optical fiber (POF), depending on a variety of factors, including but not limited to transmission rate, bandwidth of transmission, spectral width of transmission, distance of transmission, diameter of cable, cost, optical signal distortion tolerance and signal attenuation, etc. Moreover, light delivery and collection may be accomplished with other devices, such as air-core fibers, hollow waveguides, liquid waveguides and the like.

To keep the collection openings 87 of the tip electrode 37 generally free from obstruction from blood or other bodily fluids and tissue encountered by the tip electrode 37, the tip electrode is irrigated with fluid, e.g., saline, that is fed into the hollow cavity by an irrigation tube segment 48, as shown in FIG. 4A. The tube segment 48 extends through the plastic housing 21 and passage 110 in the plug 44 (FIG. 6). The distal end of the tube segment 48 is anchored in the passage 110 and the proximal end is inserted into and overlaps with a distal end of a proximal infusion tube segment 88 (FIG. 2A) that extends through the central lumen 18 of the catheter body 12 and the lumen 35 of the intermediate section 14. The proximal end of the first infusion tube segment 88 extends through the control handle 16 and terminates in a luer hub 90 (FIG. 1) or the like at a location proximal to the control handle. In practice, fluid may be injected by a pump (not shown) into the infusion tube segment 88 through the luer hub 90, and flows through the segment 88, through the infusion tube segment 48, into the hollow cavity 49 in the tip electrode 37, and out the collection openings 87. The infusion tube segments may be made of any suitable material, and is preferably made of polyimide tubing. A suitable infusion tube segment has an outer diameter of from about 0.32 inch to about 0.036 inch and an inner diameter of from about 0.14 inch to about 0.032 inch.

In accordance with a feature of the present invention, the pump maintains the fluid at a positive pressure differential relative to outside the hollow cavity 49 so as to provide a constant unimpeded flow or seepage of fluid outwardly from the hollow cavity 49 which continuously flushes the collection openings 87 and minimizes obstruction so light can freely pass through for the aforementioned light collection purposes. In addition to the above, the irrigation adaptation of the catheter 10 may serve other typical functions such as cooling the tip electrode and/or the ablation site and increasing conduction for deeper and larger lesions.

Included in the present invention is a method for manufacturing the shell 38 and inner layer 39. The method includes providing a rod of a suitable diameter and length, constructed of a suitable material that is thermally and electrically conductive which allows for radio frequency ablation using an RF generator. Such suitable material may include, without limitation, platinum-irridium, platinum, gold alloy, or palladium alloy. To form the shell 38, the distal end of the rod is turned (lathed) to form the dome shape and the interior is drilled from the proximal end. The hollow dome shell can also be formed from a flat plate which can provide a more even and smoother reflection surface with less machining and material waste. The openings 89 are drilled in the shell 38. The openings 87 may also be drilled in the shell 38. To form the inner layer 39, a moldable plastic material compounded with optical scattering material is injected or otherwise placed into the shell 38 to fill the interior of the shell and until the moldable plastic material fills and perhaps extrudes from the openings 89 in the shell 38. After the moldable plastic material sufficiently hardens, it is drilled from the proximal end of the tip electrode to form the hollow cavity 49. Alternatively, the hollow cavity shape can be incorporated into the mold so no post drilling would be needed. Smaller drill bit(s) may be used to form the distal end 92 of the cavity 49 and/or the recesses 94 in the rim region. From the exterior of the tip electrode, collection openings 87 are drilled and/or extended through the inner layer 39 and into the hollow cavity. The coating 103 made of any suitable biocompatible material is applied to the inner surface 91 of the inner layer 39 after the formation of the hollow cavity 49 with its distal end 92, but the coating may be applied before or after the formation of the recesses 94 if the recesses are masked off. If appropriate, hardened moldable plastic material extruding from openings 89 in the shell may be milled or sanded down to be flush with the outer surface of the shell 38.

To form the plug, a rod of the aforementioned suitable material with a suitable diameter and length is provided. The passages 108, 110, 112, 114 and 116 for the fiber optic cables are drilled. The plug is press-fitted or soldered around the periphery into the proximal opening of the tip electrode, but preferably after the fiber optic cables are inserted into the passages and received in the recesses 94 in the inner layer 39 of the tip electrode. The plug is in electrical contact with the shell 38. Glue, adhesive or the like is injected into the passages to fix the portions of the fiber optic cables extending through the passages. These fixed portions are intended to hold distal portions of the fiber optic cables stationary within the tip electrode as a measure against breakage in or detachment from the tip electrode.

A shell 38 of the tip electrode may have an actual length, i.e., from its distal end to its proximal end, between about 2.5 mm to about 8 mm. A plug 44 of the tip electrode may have an actual length, i.e., from its distal end to its proximal end, between about 1.5 mm to about 4.0 mm. The tip electrode as a combination of the shell and the plug may have an actual length, i.e., from its distal end to its proximal end, between about 3.5 mm to about 11.0 mm. Preferably the tip electrode 37 has a diameter about the same as the outer diameter of the tubing 19 of the intermediate section 14. As shown in FIGS. 4A and 4B, the tip electrode 37 and the plastic housing 21 are each attached to the plug 44 by, respectively, press-fitting or soldering, and by glue, adhesive at their interfacing surfaces.

Figure 6A:
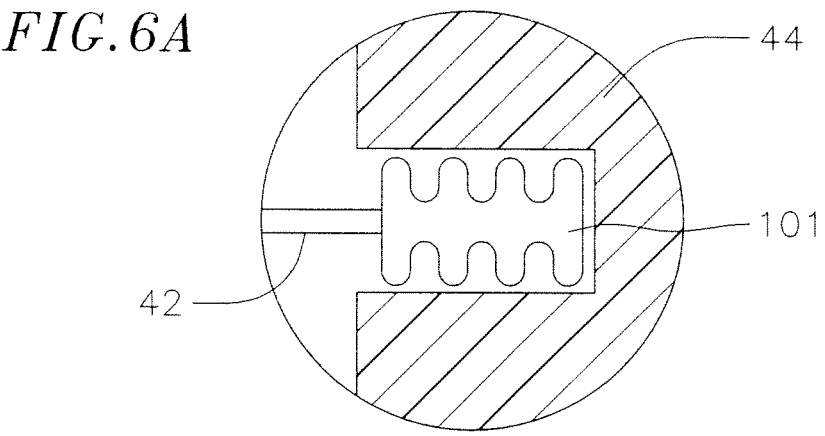
FIG. 6A is a detailed cross-sectional view of an embodiment of a lead wire.

To energize the tip electrode 37 for RF ablation, a lead wire 40 is anchored in the plug 44. With reference to FIGS. 1, 2A and 5, the lead wire 40 extends through the lumen 32 of intermediate section 14, the central lumen 18 of the catheter body 12, and the control handle 16, and terminates at its proximal end in an input jack (not shown) or connector 77 that may be plugged to an generator or the like (not shown). The portion of the lead wire 40 extending through the central lumen 18 of the catheter body 12, control handle 16 and distal end of the intermediate section 14 is enclosed within a protective sheath, which can be made of any suitable material, preferably Teflon®. The protective sheath is anchored at its distal end to the distal end of the intermediate section 14 by gluing it in the lumen 32 with polyurethane glue or the like. The lead wire 40 is attached to the tip electrode 37 by any conventional technique. In the illustrated embodiment, connection of the lead wire 40 to the tip electrode 37 is accomplished, for example, by welding the distal end of the lead wire 40 into the blind hole 102 (FIGS. 6 and 6A) in the plug 44 of the tip electrode 37.

Figure 6B:
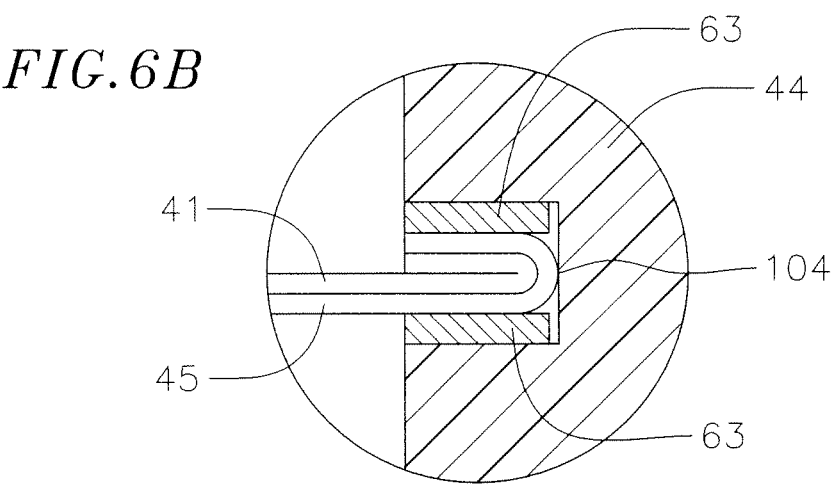
FIG. 6B is a detailed cross-sectional view of an embodiment of an anchored thermocouple wire pair.

A temperature sensing means is provided for the tip electrode 37 in the disclosed embodiment. Any conventional temperature sensing means, e.g., a thermocouple or thermistor, may be used. With reference to FIGS. 6 and 6B, a suitable temperature sensing means for the tip electrode 37 comprises a thermocouple formed by a wire pair. One wire of the wire pair is a copper wire 41, e.g., a 40 gauge or similar size copper wire. The other wire of the wire pair is a constantan wire 45, which gives support and strength to the wire pair. The wires 41 and 45 of the wire pair are electrically isolated from each other except at their distal ends where they contact and are twisted together, covered with a short piece of plastic tubing 63, e.g., polyimide, and covered with epoxy. The plastic tubing 63 is then attached in the hole 104 of the plug 44, by epoxy or the like. As shown in FIGS. 2A and 3, the wires 41 and 45 extend through the lumen 34 in the intermediate section 14. Within the catheter body 12 the wires 41 and 45 extend through the central lumen 18 within the protective sheath 52. The wires 41 and 45 then extend out through the control handle 16 and to the connector 77. Alternatively, the temperature sensing means may be a thermistor. A suitable thermistor for use in the present invention is Model No. AB6N2-GC14KA143T/37C sold by Thermometrics (New Jersey).

Referring to FIGS. 2B and 5, the puller wire 42 extends through the catheter body 12 and is anchored at its proximal end to the control handle 16. The puller wire is made of any suitable metal, such as stainless steel or Nitinol, or fiber such as Spectra or Vectran, and is preferably coated with Teflon™ or the like. The coating imparts lubricity to the puller wire. The puller wire preferably has a diameter ranging from about 0.006 to about 0.012 inches. A compression coil 56 is situated within the catheter body 12 in surrounding relation to the puller wire. The compression coil 56 extends from the proximal end of the catheter body 12 to the proximal end of the intermediate section 14. The compression coil is made of any suitable metal, preferably stainless steel, and is tightly wound on itself to provide flexibility, i.e., bending, but to resist compression. The inner diameter of the compression coil is preferably slightly larger than the diameter of the puller wire 42. The Teflon™ coating on the puller wire allows it to slide freely within the compression coil. If desired, particularly if the lead wire 40 is not enclosed by the protective sheath 52, the outer surface of the compression coils can be covered by a flexible, non-conductive sheath, e.g., made of polyimide tubing, to prevent contact between the compression coils and any other wires within the catheter body 12.

As shown in FIG. 2B, the compression coil 56 is anchored at its proximal end to the proximal end of the stiffening tube 20 in the catheter body 12 by glue joint 50 and at its distal end to the intermediate section 14 by glue joint 51. Both glue joints 50 and 51 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 and the stiffening tube 20 which is heated sufficiently to form a permanent hole. The glue is then introduced through the hole to the outer surface of the compression coil 56 and wicks around the outer circumference to form a glue joint about the entire circumference of the compression coil.

Figure 6C:
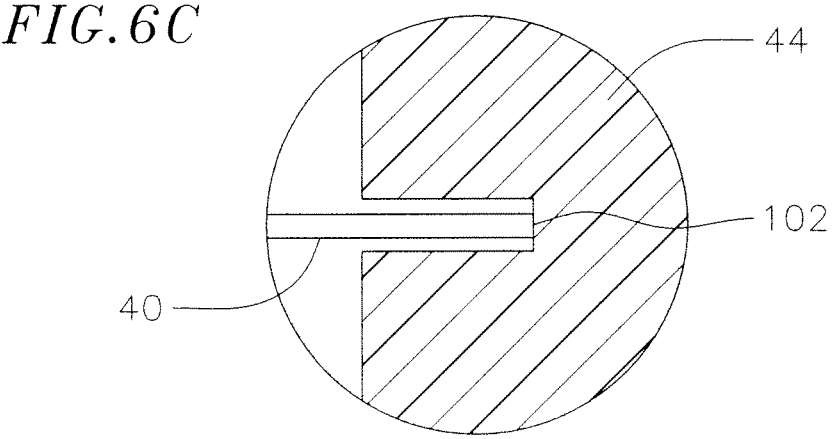
FIG. 6C is a detailed cross-sectional view of an embodiment of an anchored distal end of a puller wire.

With reference to FIGS. 2B and 5, the puller wire 42 extends into the first lumen 30 of the intermediate section 14. The puller wire 42 is anchored at its distal end to the tip electrode 37 within the blind hole 101 in the plug 44 (FIGS. 6 and 6C). A method for anchoring the puller wire 42 within the tip electrode 37 is by crimping metal tubing 46 to the distal end of the puller wire 42 and soldering the metal tubing 46 inside the blind hole 101. Anchoring the puller wire 42 within the tip electrode 37 provides additional support, reducing the likelihood that the tip electrode 37 will fall off. Alternatively, the puller wires 42 can be attached to the side of the tubing 19 at the distal end of the intermediate section 14. Within the first lumen 30 of the intermediate section 14, the puller wire 42 extends through a plastic, preferably Teflon™, sheath 81, which prevents the puller wires 42 from cutting into the wall of the intermediate section 14 when the intermediate section is deflected. Longitudinal movement of the puller wire 42 relative to the catheter body 12, which results in deflection of the tip section 36, is accomplished by suitable manipulation of the control handle 16. Suitable control handles are described in U.S. Pat. No. 6,602,242, the entire disclosure of which is hereby incorporated by reference.

In the illustrated embodiment, the tip section 36 carries an electromagnetic sensor 72, and as mentioned, the electromagnetic sensor may be carried in the plastic housing 21, with its distal end anchored in the blind hole 106 in the plug 44 as shown in FIGS. 4A, 4B and 6. The electromagnetic sensor 72 is connected to an electromagnetic sensor cable 74. As shown in FIGS. 2A and 5, the sensor cable 74 extends through the lumen 35 of the tip section 36, through the central lumen 18 of the catheter body 12, and into the control handle 16. The electromagnetic sensor cable 74 then extends out the proximal end of the control handle 16 within an umbilical cord 78 (FIG. 1) to a sensor control module 75 that houses a circuit board (not shown). Alternatively, the circuit board can be housed within the control handle 16, for example, as described in U.S. patent application Ser. No. 08/924,616, entitled "Steerable Direct Myocardial Revascularization Catheter", the disclosure of which is incorporated herein by reference. The electromagnetic sensor cable 74 comprises multiple wires encased within a plastic covered sheath. In the sensor control module 75, the wires of the electromagnetic sensor cable 74 are connected to the circuit board. The circuit board amplifies the signal received from the electromagnetic sensor 72 and transmits it to a computer in a form understandable by the computer by means of the sensor connector 77 at the proximal end of the sensor control module 75, as shown in FIG. 1. Because the catheter can be designed for single use only, the circuit board may contain an EPROM chip which shuts down the circuit board approximately 24 hours after the catheter has been used. This prevents the catheter, or at least the electromagnetic sensor, from being used twice. An electromagnetic mapping sensor 72 may have a length of from about 6 mm to about 7 mm and a diameter of about 1.3 mm.

As illustrated in FIGS. 12a-12c, an internal fixture member 200 can be positioned in the hollow cavity 49 to stabilize, secure and or protect the various fibers 43 relative to the tip electrode and shell. In the illustrated embodiment of FIG. 12b, the member 200 has a trapezoidal cross section. In the illustrated embodiment of FIG. 12c, the member 200 has an "x" cross section and a thickness t. In both embodiments, there are internal passages 202 connecting openings 204 on a surface of the member are provided through which the fibers extend from the plug 44 and toward the shell 38. The fibers can be affixed in the internal passages 202 and/or the openings 204 with glue, adhesives and the like, and/or the member 200 can be affixed by glue, adhesives and the like within the hollow cavity 49. The member can be used for electrical wires, optical fibers or any fragile tensile members 210 that are positioned in the tip electrode and can be configured with any number or patterns of passages and openings as appropriate or needed.

Figure 13:
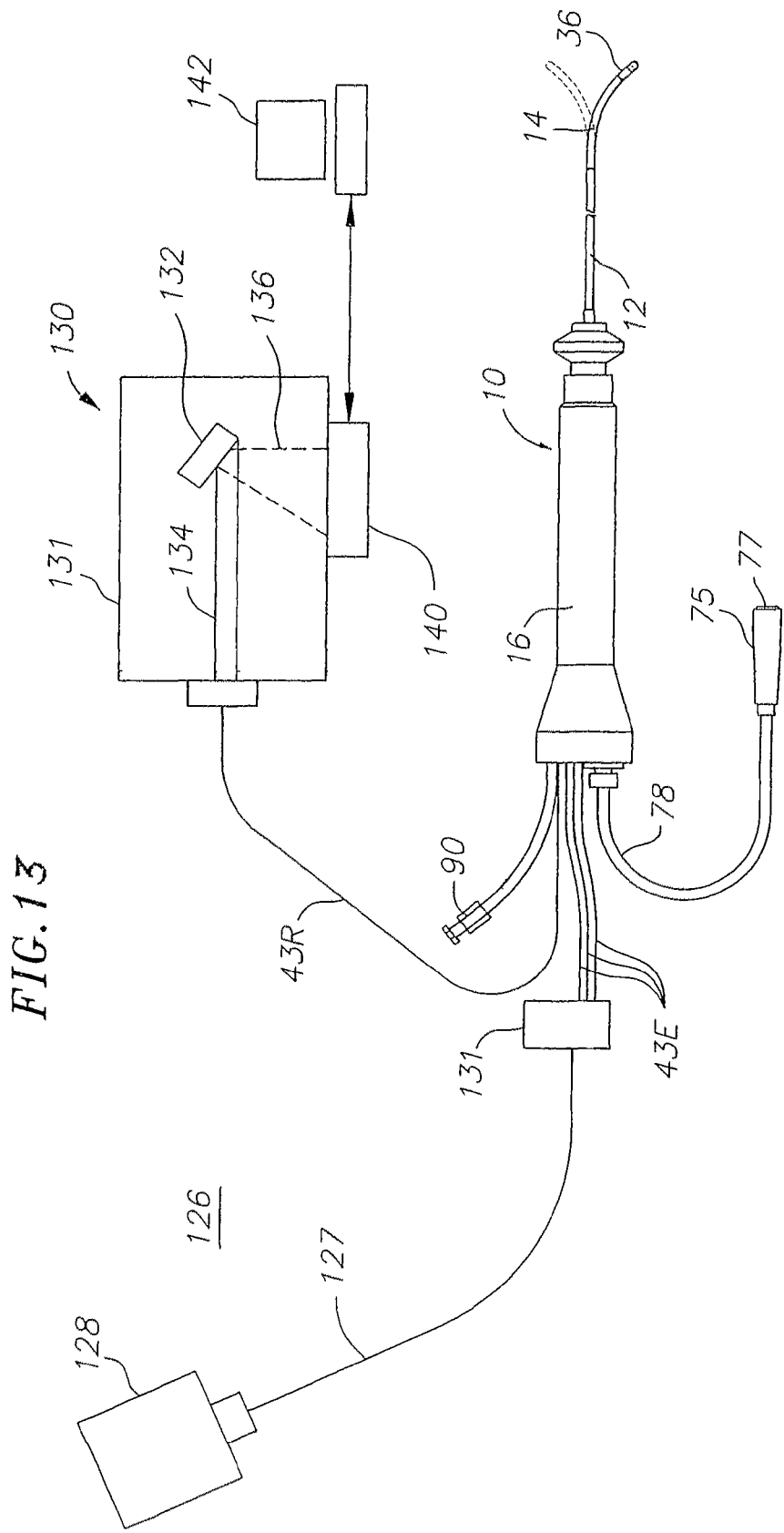
FIG. 13 is a schematic drawing showing components of an embodiment of an optical processing system for use with the catheter of the present invention.

With reference to FIG. 13, an optical processing system 126 for optically evaluating ablation tissue using the catheter 10 is illustrated. A light source 128 supplies a broadband (white; multiple wavelengths) light and/or laser light (single wavelength) radiation to the tip section 36 of the catheter 10 via cable 127 which is split by a beamsplitter 131 outputting to the emitting cables 43E. The light bearing lesion qualitative information from the tip section is transmitted by the receiving cable 43R to a detection component 130. The detection component may comprise, for example, a wavelength selective element 131 that disperses the collected light into constituent wavelengths, and a quantification apparatus 140. The at least one wavelength selective element 131 includes optics 132, as are known in the art, for example, a system of lenses, mirrors and/or prisms, for receiving incident light 134 and splitting it into desired components 136 that are transmitted into the quantification apparatus 140.

The quantification apparatus 140 translates measured light intensities into an electrical signal that can be processed with a computer 142 and displayed graphically to an operator of the catheter 10. The quantification apparatus 140 may comprise a charged coupled device (CCD) for simultaneous detection and quantification of these light intensities. Alternatively, a number of different light sensors, including photodiodes, photomultipliers or complementary metal oxide semiconductor (CMOS) detectors may be used in place of the CCD converter. Information is transmitted from the quantification device 140 to the computer 142 where a graphical display or other information is generated regarding parameters of the lesion.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:
1. A catheter, comprising:
 a catheter body;
 a tip electrode distal to the catheter body adapted for ablating tissue and obtaining optically-based data from the tissue, the tip electrode having separate optical paths for light exiting the tip electrode to illuminate tissue and light entering the tip electrode from the tissue, wherein said light entering the tip electrode from the tissue bears said optically based data, the tip electrode comprising:
an exterior shell;
a hollow cavity; and
a layer of diffuse material between an inner surface of the exterior shell and the hollow cavity, the layer of diffuse material comprising a material different from a material of the exterior shell; and
at least one opening in the exterior shell and the layer of diffuse material for receiving light from the tissue into the hollow cavity.

2. The catheter of claim 1, wherein the tip electrode has a first set of openings through which the light exiting the tip electrode passes.

3. The catheter of claim 1, wherein the at least one opening is configured to pass fluid from the hollow cavity to outside of the tip electrode.

4. The catheter of claim 1, wherein the tip electrode is illuminated by at least one fiber optic cable.

5. The catheter of claim 1, wherein the light entering the tip electrode from the tissue is received by at least one fiber optic cable.

6. The catheter of claim 1, wherein the optical path for light exiting the tip electrode includes passage through the layer of diffuse material in the tip electrode.

7. The catheter of claim 1, wherein the optical path for light entering the tip electrode from the tissue includes passage into the hollow cavity in the tip electrode.

8. The catheter of claim 6, wherein the optical path for light entering the tip electrode from the tissue includes passage into the hollow cavity in the tip electrode and the tip electrode further comprises an opaque barrier between the layer of diffuse material and the hollow cavity.

9. The catheter of claim 1, wherein fiber optic cables extend into the tip electrode to transmit light to the tip electrode from a remote light source and to transmit light from the tip electrode to an optical processing system.

10. A catheter adapted to ablate tissue, comprising:
a catheter body;
a tip electrode distal the catheter body, the tip electrode having an exterior shell, an inner layer of diffuse material and a hollow cavity, the inner layer of diffuse material comprising a material different from a material of the exterior shell, the inner layer of diffuse material being between the exterior shell and the hollow cavity and configured to transmit light to tissue outside the tip electrode via a first set of openings in the exterior shell, the hollow cavity configured to receive light from the tissue via a second set of openings in the exterior shell and the inner layer of diffuse material;
a first optical waveguide extending between the catheter body and the tip electrode to provide light into the inner layer of diffuse material;
a second optical waveguide extending between the catheter body and the tip electrode to collect light in the hollow cavity.

11. The catheter of claim 10, wherein the inner layer of diffuse material has projections that extend into the first set of openings in the exterior shell.

12. The catheter of claim 10, wherein the tip electrode is adapted for RF ablation.

13. The catheter of claim 10, wherein the second set of openings is configured to pass fluid from the hollow cavity to outside of the tip electrode.

14. The catheter of claim 10, wherein an inner surface of the inner layer of diffuse material has a coating to isolate light injected into the inner layer of diffuse material from light collected in the hollow cavity.

15. The catheter of claim 10, wherein the tip electrode has a distal section that is generally perpendicular to a longitudinal axis of the tip electrode, a mid-section that is at an angle between about 30 and 60 degrees with the longitudinal axis, and a proximal section that is generally parallel with the longitudinal axis.

16. The catheter of claim 15, wherein the angle of the mid-section is about 45 degrees.

17. The catheter of claim 15, wherein said first set of openings is configured in the mid-section and the proximal section.

18. The catheter of claim 15, wherein said second set of openings is configured in the distal and proximal sections.

19. The catheter of claim 10, further comprising a deflectable intermediate section between the catheter body and the tip electrode.

20. The catheter of claim 10, wherein the hollow cavity has a conical distal portion.

21. The catheter of claim 10, further comprising a temperature sensor.

22. The catheter of claim 10, further comprising a location sensor.

23. A method of making a tip electrode, comprising:
providing a shell having a wall defining an open proximal end and a generally dome shaped distal end;
configuring a first set of openings through the shell wall;
filling the shell with a diffuse material, the diffuse material comprising a material different from a material of the shell wall;
configuring a hollow cavity at the distal end of the shell such that the diffuse material forms a layer between the shell wall and the hollow cavity; and
configuring a second set of openings through the shell wall and the diffuse material into the hollow cavity.

24. The method of claim 23, further comprising inserting a fiber optic cable into the diffuse material to transmit light into the diffuse material.

25. The method of claim 23, further comprising inserting a fiber optic cable into the hollow cavity to collect light in the hollow cavity.

26. The method of claim 23, further comprising:
providing a plug to seal the hollow cavity;
configuring the plug with passages for a first fiber optic cable to pass into the diffuse material to transmit light into the diffuse material and a second fiber optic cable to pass into the hollow cavity to collect light in the hollow cavity.

27. The method of claim 26, further comprising fixedly securing portions of the first and second fiber optic cables in the passages.

28. The method of claim 23, wherein the shell is made of thermally and electrically conductive material.

29. The method of claim 23, further comprising coating an inner surface of the diffuse material with an opaque material.

* * * * *